(12) United States Patent
Patil et al.

(10) Patent No.: US 10,799,723 B2
(45) Date of Patent: Oct. 13, 2020

(54) ULTRASOUND DEVICE FOR SONOTHROMBOLYSIS THERAPY

(71) Applicant: KONINKLIJKE PHILIPS N.V., Eindhoven (NL)

(72) Inventors: Abhay Vijay Patil, Eindhoven (NL); Patrick G. Rafter, Eindhoven (NL); Robert L. Burnham, Eindhoven (NL); Michael Peszynski, Eindhoven (NL); Jeanne Cheng, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 524 days.

(21) Appl. No.: 15/526,353

(22) PCT Filed: Nov. 2, 2015

(86) PCT No.: PCT/IB2015/058450
§ 371 (c)(1),
(2) Date: May 12, 2017

(87) PCT Pub. No.: WO2016/075586
PCT Pub. Date: May 19, 2016

(65) Prior Publication Data
US 2017/0312548 A1 Nov. 2, 2017

Related U.S. Application Data

(60) Provisional application No. 62/079,768, filed on Nov. 14, 2014, provisional application No. 62/215,774, filed on Sep. 9, 2015.

(51) Int. Cl.
*A61N 7/00* (2006.01)
*A61B 34/00* (2016.01)
(Continued)

(52) U.S. Cl.
CPC ............... *A61N 7/00* (2013.01); *A61B 34/25* (2016.02); *A61N 1/046* (2013.01); *A61N 1/3904* (2017.08);
(Continued)

(58) Field of Classification Search
CPC ........ A61N 7/00; A61N 1/046; A61N 1/3904; A61N 2007/0052; A61N 2007/0086; A61B 34/25; A61B 2034/252; A61B 2018/00345
(Continued)

(56) References Cited

U.S. PATENT DOCUMENTS 5,509,896 A * 4/1996 Carter .............. A61B 17/22004
601/2
6,575,922 B1 6/2003 Fearnside et al.
(Continued)

FOREIGN PATENT DOCUMENTS

CN 203598374 U 5/2014
JP 2010205100 A 9/2010
(Continued)

OTHER PUBLICATIONS

Nelson ["Ultrasound Biosafety Considerations for the Practicing Sonographer and Sonologist" J Ultrasound Med 2009; 28:139-150]. (Year: 2009).*

*Primary Examiner* — Oommen Jacob

(57) ABSTRACT

A medical imaging system configured to provide cardiac sonothrombolysis therapy is disclosed. Various embodiments of portable cardiac sonothrombolysis devices are disclosed. The devices may be configured to determine if one or more ultrasound probes have a proper view of the heart, and if not, may steer the beam to a desired location. The ultrasound probes may be configured for both imaging and cardiac sonothrombolysis therapy. The ultrasound (Continued)

probes may be configured to be hands-free. The portable devices may be configured to provide operating instructions to an operator. The instructions may be provided via graphics, audio, and/or video.

3 Claims, 8 Drawing Sheets

(51) Int. Cl.
    *A61N 1/39*     (2006.01)
    *A61N 1/04*     (2006.01)
    *A61B 18/00*     (2006.01)

(52) U.S. Cl.
    CPC ............ *A61B 2018/00345* (2013.01); *A61B 2034/252* (2016.02); *A61N 2007/0052* (2013.01); *A61N 2007/0086* (2013.01)

(58) Field of Classification Search
    USPC ......................................................... 601/1, 2
    See application file for complete search history.

(56) References Cited

U.S. PATENT DOCUMENTS

| | | | |
|---|---|---|---|
| 6,733,450 B1* | 5/2004 | Alexandrov | A61N 7/00 600/439 |
| 7,165,451 B1* | 1/2007 | Brooks | A61B 8/00 73/579 |
| 7,425,198 B2 | 9/2008 | Moehring | A61B 8/06 600/454 |
| 7,850,626 B2* | 12/2010 | Vaezy | A61B 8/08 600/101 |
| 8,428,687 B2* | 4/2013 | Konofagou | A61B 5/055 600/407 |
| 2002/0072691 A1 | 6/2002 | Thompson et al. | |
| 2002/0091339 A1* | 7/2002 | Horzewski | A61N 7/00 601/2 |
| 2002/0138003 A1 | 9/2002 | Bukshpan | |
| 2002/0193708 A1* | 12/2002 | Thompson | A61N 7/00 601/2 |
| 2003/0153823 A1* | 8/2003 | Geiser | G06T 7/0012 600/407 |
| 2004/0102703 A1* | 5/2004 | Behren | A61B 8/00 600/443 |
| 2004/0127798 A1* | 7/2004 | Dala-Krishna | A61B 8/065 600/450 |
| 2004/0138563 A1* | 7/2004 | Moehring | A61B 8/06 600/439 |
| 2005/0080469 A1* | 4/2005 | Larson | A61N 7/02 607/101 |
| 2005/0203399 A1* | 9/2005 | Vaezy | A61B 8/08 600/439 |
| 2005/0222625 A1* | 10/2005 | Laniado | A61N 2/02 607/2 |
| 2006/0020210 A1* | 1/2006 | Mendlein | A61B 8/0858 600/459 |
| 2006/0025683 A1 | 2/2006 | Hoffmann | |
| 2006/0058680 A1* | 3/2006 | Solomon | A61B 8/0833 600/466 |
| 2006/0211955 A1 | 9/2006 | Horzewski et al. | |
| 2006/0241522 A1* | 10/2006 | Chandraratna | A61H 23/0245 601/2 |
| 2007/0010805 A1* | 1/2007 | Fedewa | A61N 7/02 606/27 |
| 2007/0167798 A1 | 7/2007 | Cai et al. | |
| 2008/0125657 A1* | 5/2008 | Chomas | A61N 7/00 600/458 |
| 2008/0200806 A1* | 8/2008 | Liu | A61N 7/02 600/439 |
| 2008/0262350 A1* | 10/2008 | Unger | A61B 5/6814 600/439 |
| 2008/0267509 A1* | 10/2008 | Springorum | G06T 7/68 382/201 |
| 2008/0286327 A1* | 11/2008 | Whitehurst | A61N 1/3629 424/423 |
| 2009/0141957 A1 | 6/2009 | Yen et al. | |
| 2009/0299175 A1* | 12/2009 | Bernstein | A61B 5/05 600/425 |
| 2010/0010393 A1 | 1/2010 | Duffy et al. | |
| 2010/0114254 A1* | 5/2010 | Kornet | A61N 1/36114 607/62 |
| 2010/0143241 A1* | 6/2010 | Johnson | A61K 41/0028 424/1.11 |
| 2010/0160779 A1* | 6/2010 | Browning | A61B 5/02007 600/439 |
| 2010/0179428 A1* | 7/2010 | Pedersen | A61B 8/00 600/443 |
| 2010/0280373 A1* | 11/2010 | Fan | A61B 8/0833 600/439 |
| 2011/0082371 A1* | 4/2011 | Chono | A61B 6/5217 600/443 |
| 2011/0201935 A1* | 8/2011 | Collet-Billon | A61B 8/0833 600/443 |
| 2012/0083717 A1 | 4/2012 | Alleman et al. | |
| 2012/0150038 A1* | 6/2012 | Osawa | G01S 7/5208 600/443 |
| 2012/0157842 A1* | 6/2012 | Davis | A61N 7/02 600/439 |
| 2012/0179073 A1 | 7/2012 | Nita | |
| 2012/0283605 A1* | 11/2012 | Lewis, Jr. | A61N 7/00 601/2 |
| 2013/0035582 A1* | 2/2013 | Radulescu | A61N 7/02 600/411 |
| 2013/0226001 A1* | 8/2013 | Steen | A61B 8/4427 600/447 |
| 2013/0289411 A1* | 10/2013 | Barnard | A61B 8/42 600/459 |
| 2013/0338544 A1 | 12/2013 | Newell | |
| 2014/0276247 A1 | 9/2014 | Hall et al. | |
| 2016/0129233 A1* | 5/2016 | Hoffmann | A61H 23/0263 604/22 |
| 2017/0312548 A1* | 11/2017 | Patil | A61N 1/3904 |

FOREIGN PATENT DOCUMENTS

| | | |
|---|---|---|
| WO | 0215768 A2 | 2/2002 |
| WO | 2004035138 A1 | 4/2004 |
| WO | 2007058835 A2 | 5/2007 |
| WO | 2009149390 A1 | 12/2009 |
| WO | 2012042423 A1 | 4/2012 |

\* cited by examiner

ULTRASOUND DEVICE FOR SONOTHROMBOLYSIS THERAPY

This application is the U.S. National Phase application under 35 U.S.C. § 371 of International Application No. PCT/IB2015/058450, filed on Nov. 2, 2015, which claims the benefit of Provisional Application Ser. Nos. 62/079,768 filed Nov. 14, 2014 and 62/215,774 filed Sep. 9, 2015. These applications are hereby incorporated by reference herein.

BACKGROUND

This invention relates generally to ultrasound, and more specifically to an ultrasound apparatus for sonothrombolysis therapy and methods of operation.

Sonothrombolysis is the dissolution of thrombus by low-power and low-frequency acoustic pulses. Medical studies have shown that low-power, low-frequency ultrasound pulses applied to cardiac tissue may improve microvascular and epicardial blood flow and improve perfusion of tissue, including cardiac tissue. The improvements in blood flow and perfusion are believed to be due to the ultrasound-induced dissolving of thrombi and triggering of vasodilation in the microvasculature. These effects may be observed with ultrasound applied alone, and may optionally be enhanced by the presence of microbubbles and/or combined with drug therapy.

Cardiac sonothrombolysis may have a therapeutic effect for cardiovascular disease. It may be used as a treatment for chronic cardiovascular disease and/or acute cardiac events. In particular, some studies suggest that sonothrombolysis during a myocardial infarction may prevent post-infarction complications. In some cases, it may increase the nutrient supply to starving myocardial muscle. This may reduce the extent of tissue death due to a myocardial infarction and may also increase the time window in which another medical intervention may be effective. For example, emergency angioplasty, stent placement, and/or coronary bypass surgery may be delayed if a patient is treated with sonothrombolysis. This may improve patient outcomes, especially for patients who experience a myocardial infarction in a remote area and/or a clinic without interventional cardiology capabilities immediately available.

Currently, cardiac sonothrombolysis is typically an experimental procedure that requires a clinical environment with extensive equipment, skilled sonographers and clinicians. This may limit the use of cardiac sonothrombolysis as an effective treatment for acute cardiac events, which often occur outside a clinical setting.

SUMMARY

According to one illustrative embodiment disclosed, a medical imaging system may include an ultrasound probe which may be configured to acquire a signal and deliver a low power ultrasound therapy, an image processor which may be configured to receive the signal from the ultrasound probe, a heart recognition processor which may be configured to determine if the ultrasound probe has a desired view of a heart, based, at least in part, on data received from the image processor, and a transmit controller which may be configured to steer a beam of the ultrasound probe and control delivery of the low power ultrasound therapy. The ultrasound probe may include a housing, an ultrasound transducer enclosed in the housing, and a holding socket that may at least partially enclose the housing. The holding socket may include a rim surrounding an outer perimeter of the housing. The ultrasound probe may further include an adhesive on the rim, which may be configured to couple the ultrasound probe to a surface.

According to another illustrative embodiment disclosed, a cardiac sonothrombolysis device may include an ultrasound probe which may be configured to acquire a signal and deliver a low power ultrasound therapy, and a computer coupled to the ultrasound probe. The computer may include an image processor which may be configured to receive the signal from the ultrasound probe, a blockage detector processor which may be configured to determine if an object is blocking a field of view of the ultrasound probe, based, at least in part, on data received from the image processor, a heart recognition processor which may be configured to determine if the ultrasound probe has a desired view of a heart, based, at least in part, on data received from the image processor, and a transmit controller which may be configured to steer a beam of the ultrasound probe and control delivery of the low power ultrasound therapy. The computer may be a tablet computer which may include a touch-screen. The computer may communicate wirelessly with the ultrasound probe.

According to a further illustrative embodiment disclosed, a method may include receiving a signal from an ultrasound probe; analyzing the signal with a blockage detector processor to determine if a an object is blocking a field of view of the ultrasound probe; analyzing the signal with a heart recognition processor to determine if the ultrasound probe has a desired view of a heart; steering a beam of the ultrasound probe responsive to determining an object is blocking the field of view or the ultrasound probe does not have the desired view of the heart; and providing cardiac sonothrombolysis therapy with the ultrasound probe. The method may further include providing instructions for placing the ultrasound probe on a patient to a user. The method may further include providing external defibrillation with an electrode.

DETAILED DESCRIPTION

Figure 1:
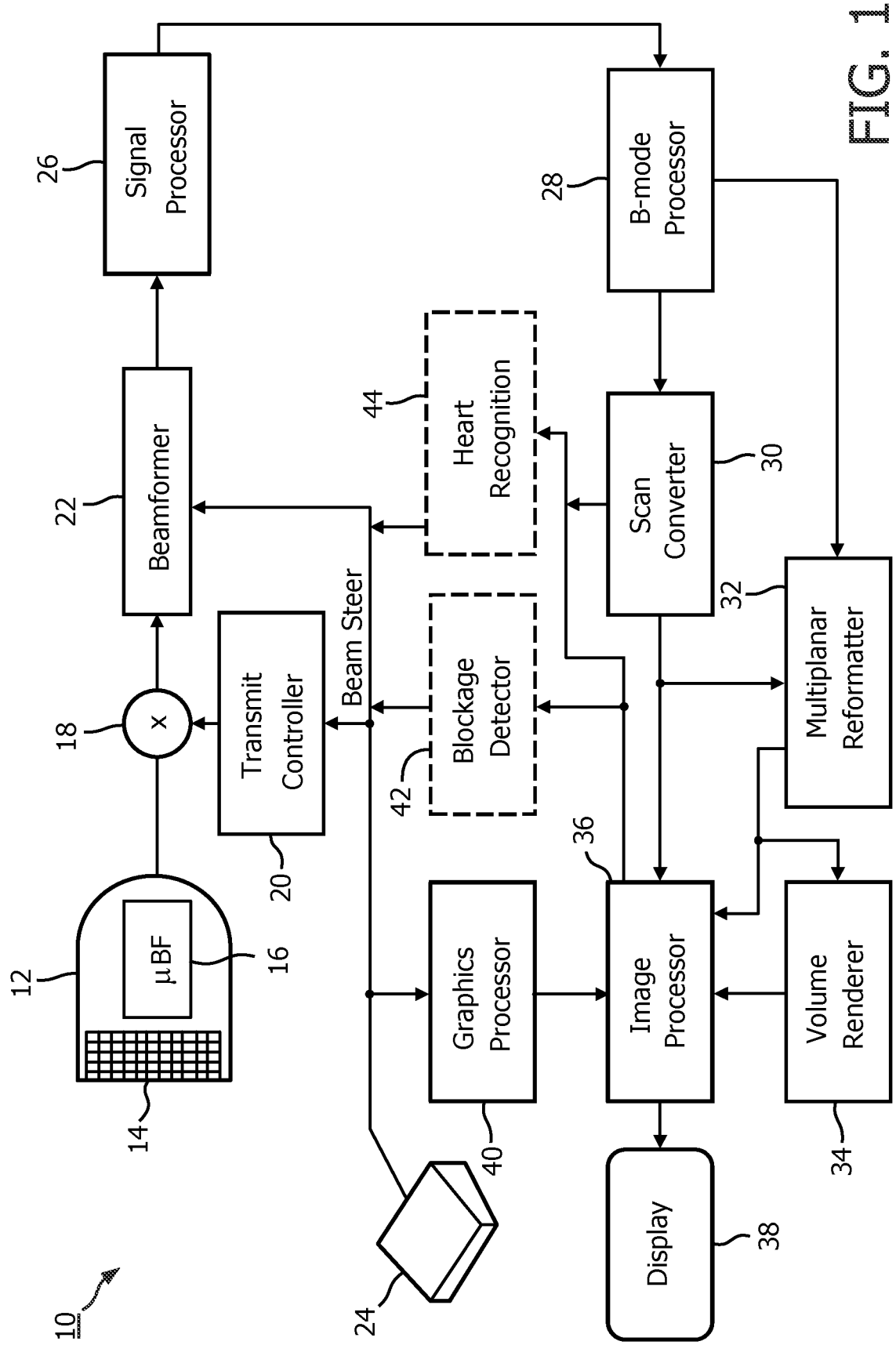
FIG. 1 is a block diagram of an ultrasound imaging system according to an embodiment of the disclosure.

The following description of certain exemplary embodiments is merely exemplary in nature and is in no way intended to limit the invention or its applications or uses. In the following detailed description of embodiments of the present systems and methods, reference is made to the accompanying drawings which form a part hereof, and in which are shown by way of illustration specific embodiments in which the described systems and methods may be practiced. These embodiments are described in sufficient detail to enable those skilled in the art to practice the presently disclosed systems and methods, and it is to be understood that other embodiments may be utilized and that structural and logical changes may be made without departing from the spirit and scope of the present system.

The following detailed description is therefore not to be taken in a limiting sense, and the scope of the present system is defined only by the appended claims. The leading digit(s) of the reference numbers in the figures herein typically correspond to the figure number, with the exception that identical components which appear in multiple figures are identified by the same reference numbers. Moreover, for the purpose of clarity, detailed descriptions of certain features will not be discussed when they would be apparent to those with skill in the art so as not to obscure the description of the present system.

Described herein are various embodiments of systems, applications and/or methods for providing sonothrombolysis therapy with a portable device to a patient. In some applications, the patient may be experiencing a cardiac event. In some applications, the patient may be experiencing other vascular circulation difficulties such as a blood clot or stenosis. While sonothrombolysis systems and methods will be described with reference to cardiac sonothrombolysis (CS) systems and methods, it will be appreciated that sonothrombolysis may be applied to other areas of the body, for example, stenosis of carotid arteries and leg blood clots. The description of various embodiments of cardiac thrombolysis systems and methods is not intended to limit the scope of the present invention to merely CS systems and methods. In some embodiments, the system may include two ultrasound probes coupled to a hand-held system. In some embodiments, the system may be configured to be used in a non-clinical setting. Accordingly, it may be possible to provide CS therapy to a patient experiencing an acute cardiac event before and/or during transport to a medical facility. This may reduce post-infarction complications and improve patient outcomes.

In some embodiments, a portable CS device may be configured for use by emergency medical responders (EMRs) (e.g., paramedics, emergency medical technicians, fire fighters). The portable CS device may provide instructions for use to the EMRs via graphics, an electronic display, audio, audio and/or video. EMRs may respond to a medical emergency and determine that a patient is experiencing an acute cardiac event, for example, a myocardial infarction. The EMRs may choose to treat the patient with the portable CS device. The portable CS device may guide the placement of two or more ultrasound probes at appropriate locations on the patient to provide cardiac sonothrombolysis therapy. The ultrasound probes may include an adhesive such that the probes remain in position once placed by the EMRs. Once the ultrasound probes have been placed, the CS device may automatically treat the patient. In some embodiments, the CS device may guide the EMRs to perform further actions to provide CS therapy. In some embodiments, the CS device may be used by the EMRs in conjunction with an automatic defibrillator device. In some embodiments, the CS device and the AED may be included in a single device. The EMRs may continue treatment of the patient with the CS device during other treatments to the patient (e.g., oxygen, aspirin, CPR) and transport to a medical facility. Providing a device that may enable EMRs to administer CS therapy to a patient may increase the time window in which the patient may receive effective interventions that require a medical facility.

In some embodiments, a device and/or system for providing cardiac sonothrombolysis therapy may be included in or coupled to a conventional ultrasound imaging system used in a clinical environment. The device may provide easier detection of the area to be treated and target delivery to the appropriate area. This may allow greater patient access to CS therapy and reduced variance in effectiveness of CS in patients. A device in a clinical environment may be used for treatment of both chronic and acute cardiovascular disease.

Referring to FIG. 1, an ultrasound imaging system 10 constructed in accordance with the principles of the present invention is shown in block diagram form. In the ultrasonic diagnostic imaging system of FIG. 1, an ultrasound probe 12 includes a transducer array 14 for transmitting ultrasonic waves and receiving echo information. A variety of transducer arrays are well known in the art, e.g., linear arrays, convex arrays, matrix arrays, or phased arrays. The transducer array 14, for example, can include a two dimensional array (as shown) of transducer elements capable of scanning in both elevation and azimuth dimensions for 2D and/or 3D imaging. Elements of the array can include, e.g., piezoelectric elements or capacitive micromachined transducers (CMUTs). The transducer array 14 is coupled to a microbeamformer 16 in the probe 12 which controls transmission and reception of signals by the transducer elements in the array. In this example, the microbeamformer is coupled by the probe cable to a transmit/receive (T/R) switch 18, which switches between transmission and reception and protects the main beamformer 22 from high energy transmit signals. In some embodiments, the T/R switch 18 and other elements in the system can be included in the transducer probe rather than in a separate ultrasound system base. The transmission of ultrasonic beams from the transducer array 14 under control of the microbeamformer 16 is directed by the transmit controller 20 coupled to the T/R switch 18 and the beamformer 22, which receives input from the user's operation of the user interface or control panel 24. One of the functions controlled by the transmit controller 20 is the direction in which beams are steered. Beams may be steered straight ahead from (orthogonal to) the transducer array, or at different angles for a wider field of view. The transmit controller 20 may recalculate and/or select a sequence of focusing coefficients for transmit and receive beamforming in the directions needed to scan a desired plane in a location specified by a user and/or another processor included in the ultrasound system 10. This steering of the image plane may allow multiple areas of the body to be imaged and/or exposed to ultrasound therapy without physically moving the ultrasound probe 12. The partially beamformed signals produced by the microbeamformer 16 are coupled to a main beamformer 22 where partially beamformed signals from individual patches of transducer elements are combined into a fully beamformed signal.

The beamformed signals are coupled to a signal processor 26. The signal processor 26 can process the received echo signals in various ways, such as bandpass filtering, decimation, I and Q component separation, and harmonic signal separation. The signal processor 26 may also perform additional signal enhancement such as speckle reduction, signal compounding, and noise elimination. The processed signals are coupled to a B mode processor 28, which can employ amplitude detection for the imaging of structures in the body. The signals produced by the B mode processor are coupled to a scan converter 30 and a multiplanar reformatter 32. The scan converter 30 arranges the echo signals in the spatial relationship from which they were received in a desired image format. For instance, the scan converter 30 may arrange the echo signal into a two dimensional (2D) sector-shaped format, or a pyramidal three dimensional (3D) image. The multiplanar reformatter 32 can convert echoes which are received from points in a common plane in a volumetric region of the body into an ultrasonic image of that plane, as described in U.S. Pat. No. 6,443,896 (Detmer). A volume renderer 34 converts the echo signals of a 3D data set into a projected 3D image as viewed from a given reference point, e.g., as described in U.S. Pat. No. 6,530,885 (Entrekin et al.) The 2D or 3D images are coupled from the scan converter 30, multiplanar reformatter 32, and volume renderer 34 to an image processor 36 for further enhancement, buffering and temporary storage for display on an image display 38. The graphics processor 36 can generate graphic overlays for display with the ultrasound images. These graphic overlays can contain, e.g., standard identifying information such as patient name, date and time of the image, imaging parameters, and the like. For these purposes the graphics processor receives input from the user interface 24, such as a typed patient name. The user interface can also be coupled to the multiplanar reformatter 32 for selection and control of a display of multiple multiplanar reformatted (MPR) images.

Although the ultrasound system 10 as described above may be capable of providing cardiac sonothrombolysis (CS) therapy according to an embodiment of the invention, the ultrasound system 10 may also include additional elements that may provide additional functionality. As will be described below, the additional functionality may allow a clinician that is not a skilled sonographer to provide more consistent CS therapy.

In some embodiments, the ultrasound system 10 may include a blockage detector processor 42. The blockage detector processor 42 may receive data from the image processor 36 and/or the scan converter 30. The blockage detector processor 42 may determine when an object is blocking the field of view of the ultrasound probe 12. Possible blockages may include, but are not limited to, ribs, lungs, and implantable devices. In some embodiments, the blockage may be detected by determining the coherence of data from the individual transducer elements of the transducer array 14. "Coherence" as used herein, is meant to mean similarity among data recorded by different elements of the transducer array. One gauge of coherence is a beam summed-data-based coherence estimation method, such as the one described in U.S. Patent Publication No. 2009/0141957 to Yen et. al. Other estimation methods may also be used. The coherence estimation method chosen may be tailored to detecting rib, lung, and/or other blockages. A sharp change in intensity and/or echo delay in one or more transducer elements may indicate a blockage in the field of view of the transducer 12. The blockage detector processor 42 may further be configured to spatially define a blockage that has been detected. In some embodiments, the blockage detector processor 42 may provide an alert to a user that a blockage may be interfering with the transducer's field of view. In some embodiments, the blockage detector processor 42 may provide instructions to the transmit controller 20 to steer the beam of the ultrasound transducer 12 to avoid the blockage. The blockage detector processor 42 may reduce or eliminate the skilled micro-adjustment of the probe required to be performed by the clinician. This may allow the blockage detector processor 42 to provide more consistent unobstructed transducer fields of view.

In some embodiments, the ultrasound system 10 may include a heart recognition processor 44. The heart recognition processor 44 may receive data from the image processor 36. The heart recognition processor 44 may be configured to analyze data from the image processor 36 and determine whether the ultrasound probe 12 has the desired view of the heart. The desired view may be a complete view of the heart or a particular portion of the heart to be targeted for CS therapy. In some embodiments, the heart recognition processor 44 may send a signal to a user indicating whether or not the desired view has been achieved. In some embodiments, if the desired view of the heart is not captured, the heart recognition processor 44 may be further configured to provide instructions to the transmit controller 20 to steer the beam of the ultrasound transducer 14 to acquire the desired view of the heart. The heart recognition processor 44 may reduce or eliminate physical manipulation of the probe by the clinician in order to acquire the desired view of the heart for proper delivery of CS therapy.

The transmit controller 20 may receive control signals from the user interface 24, blockage detector processor 42, and/or heart recognition processor 44 for providing CS therapy. In some embodiments, the transmit controller 20 may include pre-existing CS therapy control signals stored in a memory (not shown). The transmit controller 20 may provide control signals to the microbeamformer 16 to provide control signals to the transducer array 14 to provide CS therapy.

In some embodiments, the ultrasound imaging system 10 shown in FIG. 1 may be an "on cart" system used in a clinical environment. An example on cart system that may be used to implement the ultrasound system 10 in some embodiments is the Philips® Sonos ultrasound system. In some embodiments, a second ultrasound probe (not shown) is coupled to the imaging system 10. The second ultrasound probe may be similar to the ultrasound probe 12. The two ultrasound probes may be matrix probes. In addition to imaging, the ultrasound probes may be configured to provide low power ultrasound therapy for sonothrombolysis. For example, the probes may be configured to provide pulses around 5-200 μs at a frequency less than or equal to 2.5 MHz with a mechanical index (MI) less than or equal to 1.9, and a spatial-peak temporal-average intensity (ISPTA) of less than or equal to 720 mW/cm$^2$. The ultrasound probes 12 may include active cooling elements (not shown) for the transducer array 14 to aid in heat dissipation.

Figure 2:
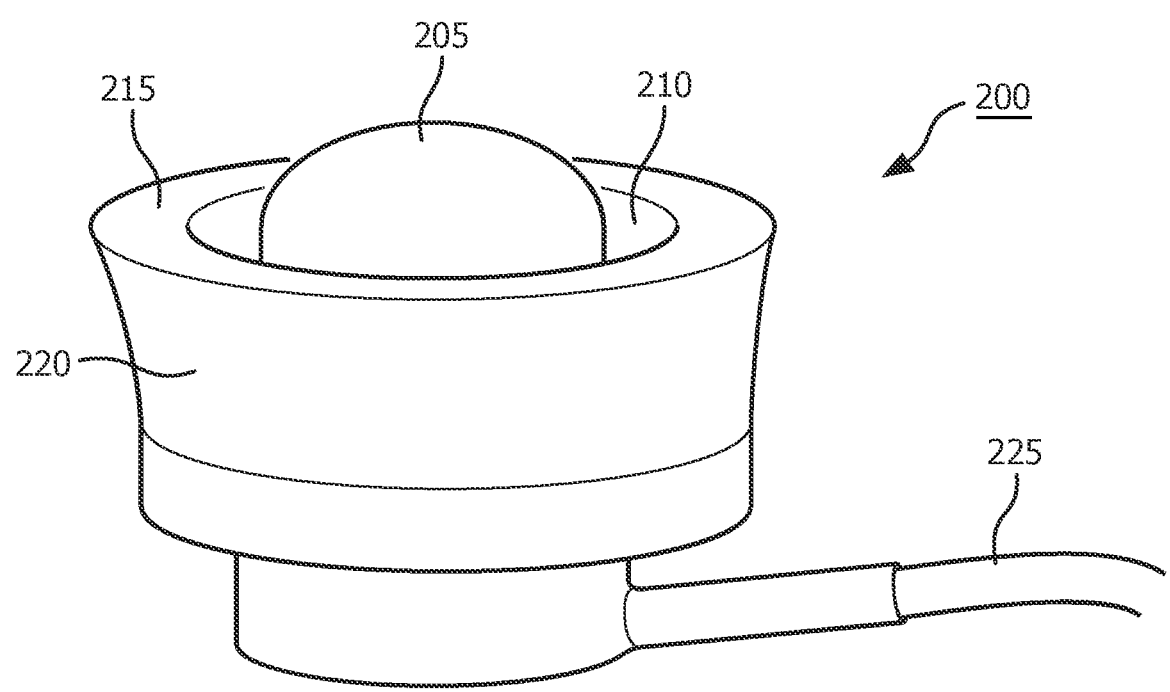
FIG. 2 is a schematic illustration of an ultrasound probe according to an embodiment of the disclosure.

FIG. 2 illustrates an example hands-free probe 200 according to an embodiment of the disclosure. The hands-free probe 200 may be used in addition to or instead of a traditional hand-held ultrasound probe to deliver CS therapy. The hands-free probe 200 may be used to implement ultrasound probe 12 in FIG. 1. If two ultrasound probes are used, both may be hands-free. The hands-free probe 200 includes a housing 205 that encloses a matrix transducer array (not shown). The matrix transducer array may be configured to have a sideward firing configuration. The sideward firing configuration may allow the transducer in the housing 205 to be coupled in a holding socket 220. Although the housing 205 is illustrated as a sphere and the holding socket 220 as a ring in FIG. 2, other shapes for the housing and holding socket may be used. The holding socket 220 may have a rim 215 that may be removably coupled to a patient's skin. The rim 215 may be coupled by an adhesive, suction, and/or another coupling method. An intermediate space 210 between the holding socket 220 and the housing 205 may be filled with a gel (not shown) which may improve acoustical coupling between the housing 205 and the patient. In some embodiments, a user may apply the gel. In some embodiments, the hands-free probe 200 may come pre-filled with gel. In some embodiments, a cable 225 may be coupled to the transducer on the opposite side of the holding socket 220 from the rim 215. The cable 225 may send and/or receive power and/or control signals from an ultrasound imaging system to the transducer. In some embodiments, the cable 225 is omitted. The hands-free probe 200 may include a battery and transmitter (not shown) and communicate wirelessly with an ultrasound imaging system. In some embodiments, the hands-free probe 200 may be configured to provide pulses around 5-200 µs at a frequency less than or equal to 2.5 MHz with a mechanical index (MI) less than or equal to 1.9, and a spatial-peak temporal-average intensity (ISPTA) of less than or equal to 720 mW/cm$^2$. The hands-free probe 200 may include active cooling elements (not shown) for the transducer array to aid in heat dissipation.

Figure 3:
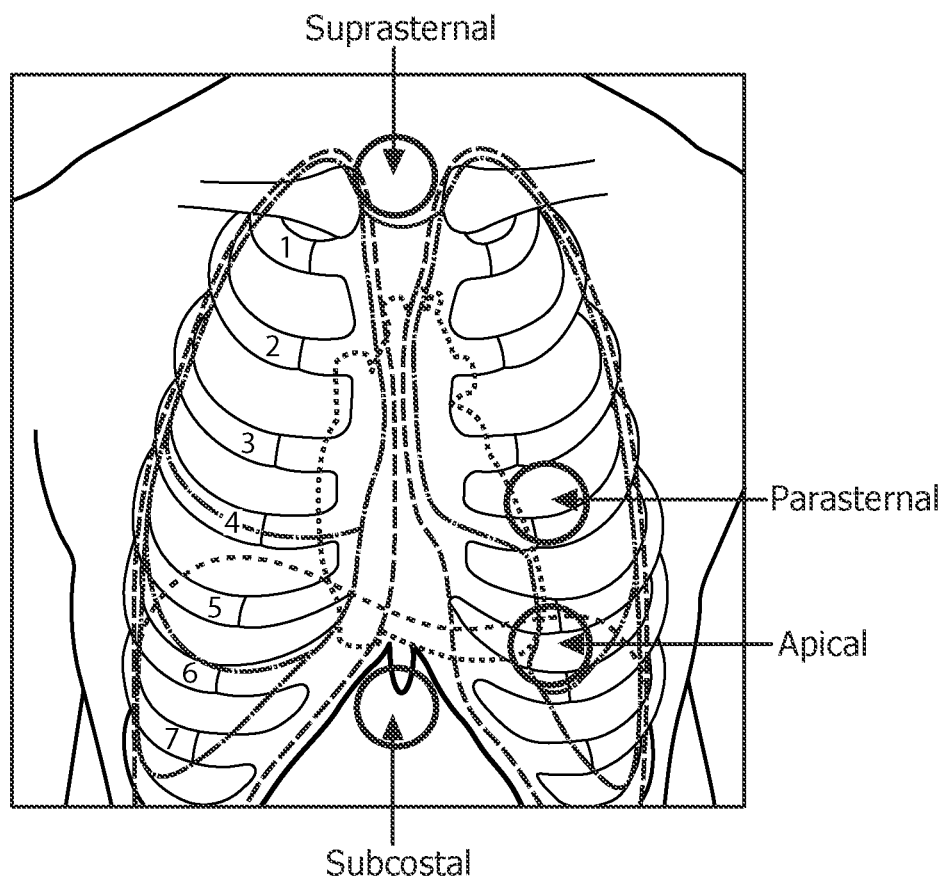
FIG. 3 is a schematic illustration of example acoustical windows.

In typical operation of an embodiment of the disclosure in a clinical environment with an on cart ultrasound system, a user may apply one or more ultrasound probes, such as the hands-free ultrasound probe illustrated in FIG. 2 to a patient's torso. FIG. 3 illustrates a diagram of possible application sites that provide acoustical windows to the heart. For example, the user may apply a probe to the apical window and the parasternal window. Other probe positioning may be used. The user may then provide the CS therapy to the patient by initiating a CS sequence on the ultrasound system via the user interface 24. In some embodiments, the user may be prompted to input certain parameters, for example, dosage, time duration, pulse sequence, and/or other parameters. In some embodiments, the ultrasound system may already be pre-programmed with parameters. In some embodiments, the user may enhance the CS therapy by administering microbubbles and/or medications to the patient before or during CS therapy. Once therapy has been delivered to the patient, the user may remove the probes.

Figure 4:
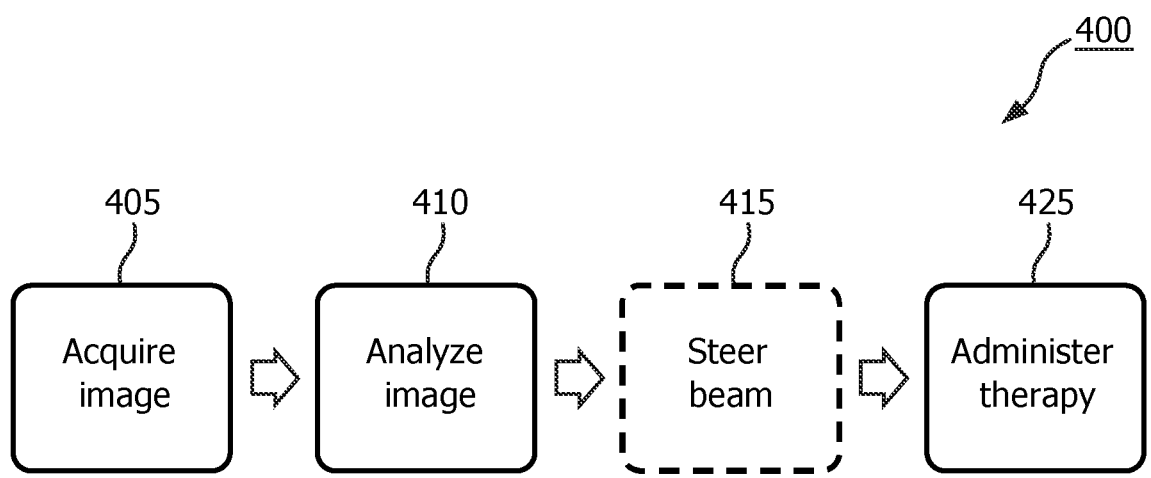
FIG. 4 is a flow chart of a method according to an embodiment of the disclosure.

FIG. 4 is a flow chart of an example process 400 performed by the ultrasound system. First, at Step 405, one or more ultrasound probes may acquire an image of the patient. The image may be analyzed by a blockage detector processor and/or a heart recognition processor at Step 410. If the analysis determines that the patient's heart is not adequately within the field of view of one or more of the ultrasound probes, the beam of one or more of the ultrasound probes may be steered to achieve adequate imaging. If the beam cannot be steered to achieve an adequate field of view, the ultrasound system may alert the user that one or more ultrasound probes need to be removed and reapplied. In some embodiments, the ultrasound system may use tractor-treading and/or a combination of beam steering and tractor treading to locate a desired field of view. After the heart has been determined to be adequately within the field of view of the one or more ultrasound probes, the ultrasound probes may then deliver CS therapy to the patient at Step 425.

In some embodiments, a device and/or system for providing cardiac sonothrombolysis may be included in a portable device for use in a non-clinical environment. For example, it may be used by emergency medical responders (EMR) in homes, businesses, or outdoors during a medical emergency. A portable CS device may be configured to be used primarily for treatment of acute cardiovascular events.

A portable CS device may include similar elements as the ultrasound imaging system 10 of FIG. 1. However, it may have reduced capabilities. For example, it may have fewer controls, options, and/or menus provided in the user interface 24. It may have no display 38 and/or a smaller display. The smaller display may be lower resolution. The portable CS device may have reduced volume rendering, image processing, and other processing capabilities typical of traditional clinical ultrasound systems. High resolution imaging, image processing, and providing images to the user may not be necessary for successfully delivering CS therapy. The reduced functionality may allow the device to be lightweight and less costly than a traditional clinical ultrasound system.

Figure 5:
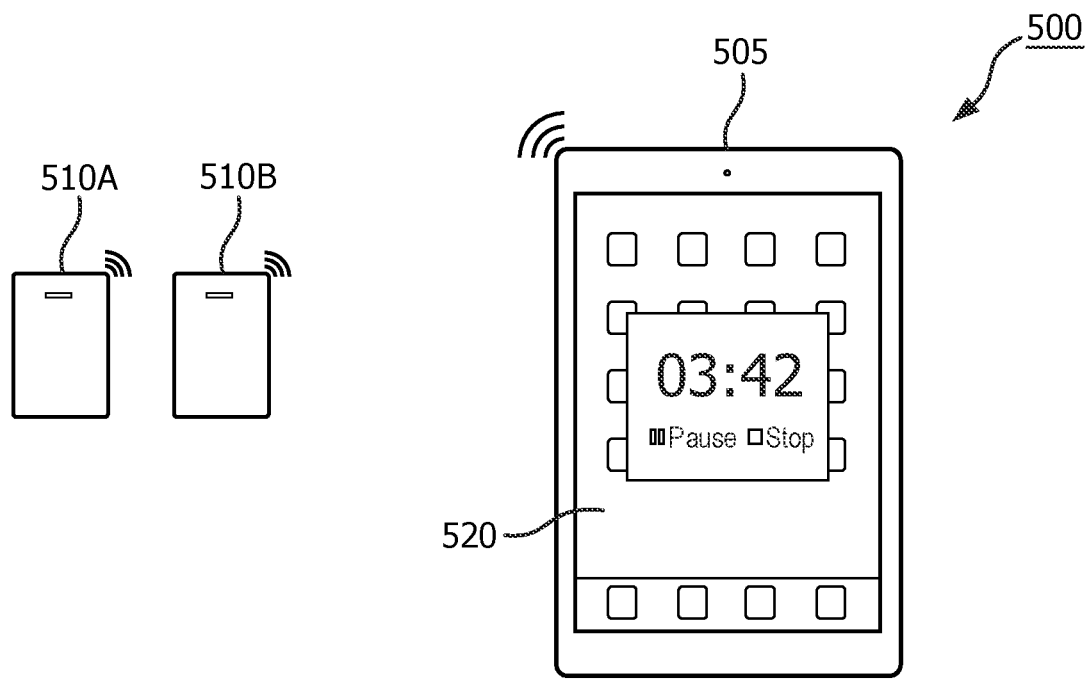
FIG. 5 is a portable cardiac sonothrombolysis (CS) device according to an embodiment of the disclosure.
Figure 6:
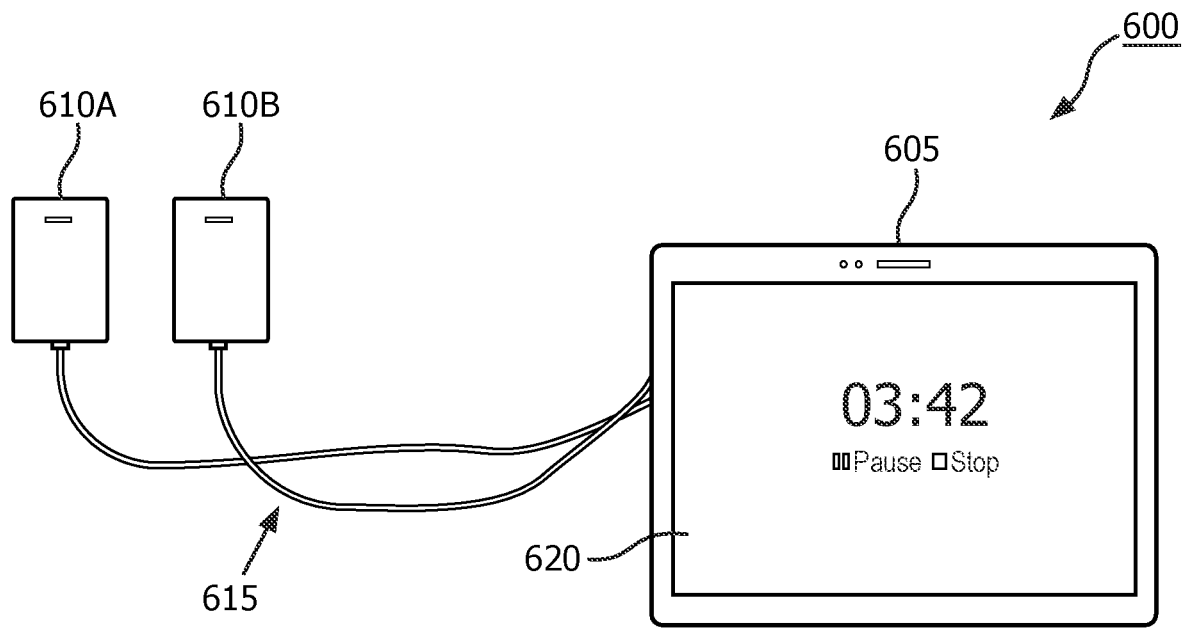
FIG. 6 is a schematic illustration of a portable CS device according to an embodiment of the disclosure.

FIGS. 5 and 6 show schematic illustrations of example portable CS devices 500, 600 according to embodiments of the disclosure. In both devices 500 and 600, a tablet computer 505, 605 may be configured to perform all or a portion of the operations of an ultrasound imaging system. For example, the tablet computer 505, 605 may include processors, controllers, and renderers for performing signal processing, beam steering, and/or other operations. An example of a tablet computer configured to perform all or a portion of the operations of an ultrasound imaging system is the Philips VISIQ ultrasound system. A user may interface with the portable CS device 500, 600 through a user interface on a touch screen 520, 620. The portable CS device 500, 600 may further include one or more ultrasound probes 510A-B, 610A-B. The ultrasound probes 510A-B, 610A-B may be implemented by the ultrasound probe 200 illustrated in FIG. 2. As shown in FIG. 5, the ultrasound probes 510A-B may be configured to communicate with the tablet 505 wirelessly in some embodiments. The ultrasound probes 510A-B may include a power source, for example, a battery and a transmitter (not shown). Alternatively, as shown in FIG. 6, ultrasound probes 610A-B may be configured to be coupled to the tablet 605 via cables 615. The tablet 605 may provide control signals and power to the ultrasound probes 610A-B via the cables 615. In some embodiments, the tablet 605 may only provide control signals via the cables 615, and the ultrasound probes 610A-B may include an independent power source, for example, a battery (not shown). In some embodiments, a portable CS device may be configured to include ultrasound probes that may operate both wirelessly and with cables, allowing the user to adapt the portable device to their preference.

An EMR treating a patient may determine an acute cardiac event has occurred. The EMR may use a portable CS device such as portable device 500 or 600. The EMR may execute an application on the tablet computer. The application may allow the EMR to control the delivery of CS therapy to the patient. In some embodiments, the application may provide visual, audio, and/or video instructions to the EMR for operating the portable device. For example, the portable CS device may instruct the EMR how to apply one or more ultrasound probes to the patient. The portable CS device may further instruct the EMR to reposition the probes if it determines the probes are not correctly placed. Once the ultrasounds have been placed correctly, the portable CS device may provide further instructions and/or options for delivering CS therapy to the EMR. The EMR may interact with the portable CS device via a touch screen interface. Other user interfaces may also be used. The EMR may manually modify the CS therapy provided by the portable CS device or the portable CS device may automatically determine the appropriate therapy. In some embodiments, the portable CS device may have both manual and automatic modes.

In some embodiments, the portable CS device may include a memory that may store a record of therapy provided to a patient. For example, the portable CS device may record date, time of treatment, duration, dosage, and/or other therapy details. The portable CS device may also allow the EMR to input additional patient information for recording in memory. Example information may include, but is not limited to, patient name, age, medication list, and known allergies. In some embodiments, the portable CS device may transmit the therapy and patient data to a remote location, for example, a hospital or doctor's office. The portable CS device may transmit the information wirelessly. In some embodiments, the EMR may bring the CS device to a computer station in an ambulance, hospital, and/or other location. The portable CS device may be coupled to the computer station and transfer the information from the memory to the computer station. This may allow clinicians treating the patient to have information regarding prior treatment provided.

Figure 7:
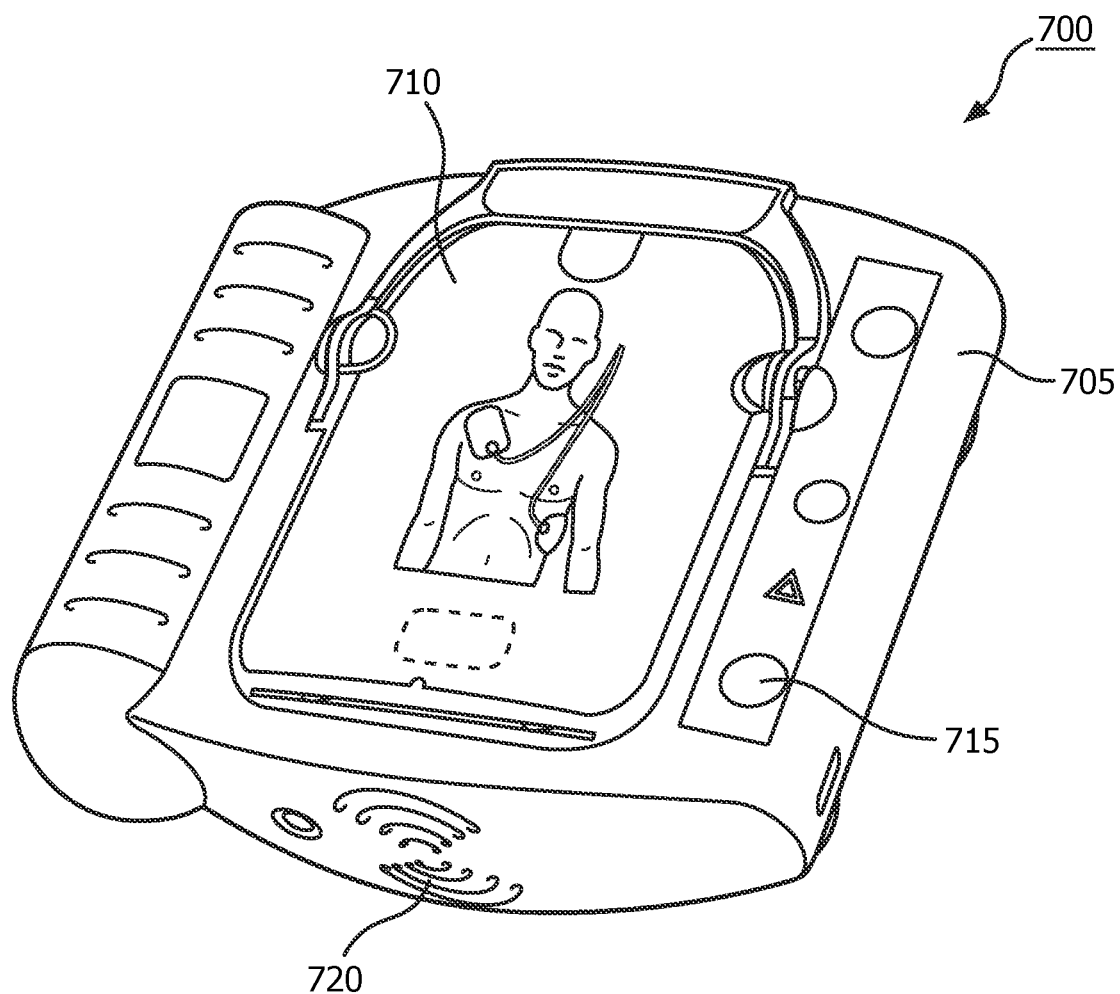
FIG. 7 is a schematic illustration of a portable CS device according to an embodiment of the disclosure.

FIG. 7 shows a schematic illustration of an example portable CS device 700 according to an embodiment of the disclosure. In some embodiments, the portable CS device 700 may be implemented as a customized circuit board including processors, controllers, and renderers configured to carry out functions for providing CS therapy. The customized circuit board may be enclosed in a rugged plastic and/or metal case 705. The portable CS device 700 may have a small display or no display. The case 705 may have printed graphical instructions 710 for using the device in addition to or instead of a display. The user interface for the portable CS device 700 may be limited to one or more buttons 715. The portable CS device 700 may further include a speaker 720 for providing audio instructions to a user. The portable CS device 700 may be coupled via cables or wirelessly to one or more ultrasound probes (not shown). The ultrasound probes may be implemented using the ultrasound probes shown in FIG. 2.

In some embodiments, a portable CS device, such as portable device 700 shown in FIG. 7 may be used by an operator such as an EMR or a person without medical training responding to a patient in distress. For example, the person may come to the aid of someone at a shopping center or a park before EMRs arrive. In some embodiments, graphics printed on the case of the portable device may instruct the operator how to turn on the portable CS device. Once powered on, the portable CS device may automatically provide graphical, audio, or video instructions to the operator for operating the portable CS device. For example, the portable CS device may instruct the operator how to apply one or more ultrasound probes to the patient. The portable CS device may further instruct the operator to reposition the probes if it determines the probes are not correctly placed. Once the ultrasound probes have been placed correctly, the portable CS device may provide further instructions to the operator to provide CS therapy. In some embodiments, once the ultrasound probes are placed correctly, the portable CS device may automatically begin providing CS therapy. In some embodiments, the portable CS device may provide additional instructions to the operator for treating the patient. For example, the portable CS device may provide instructions on emergency breathing, checking for a pulse, and/or administering CPR.

Figure 8:
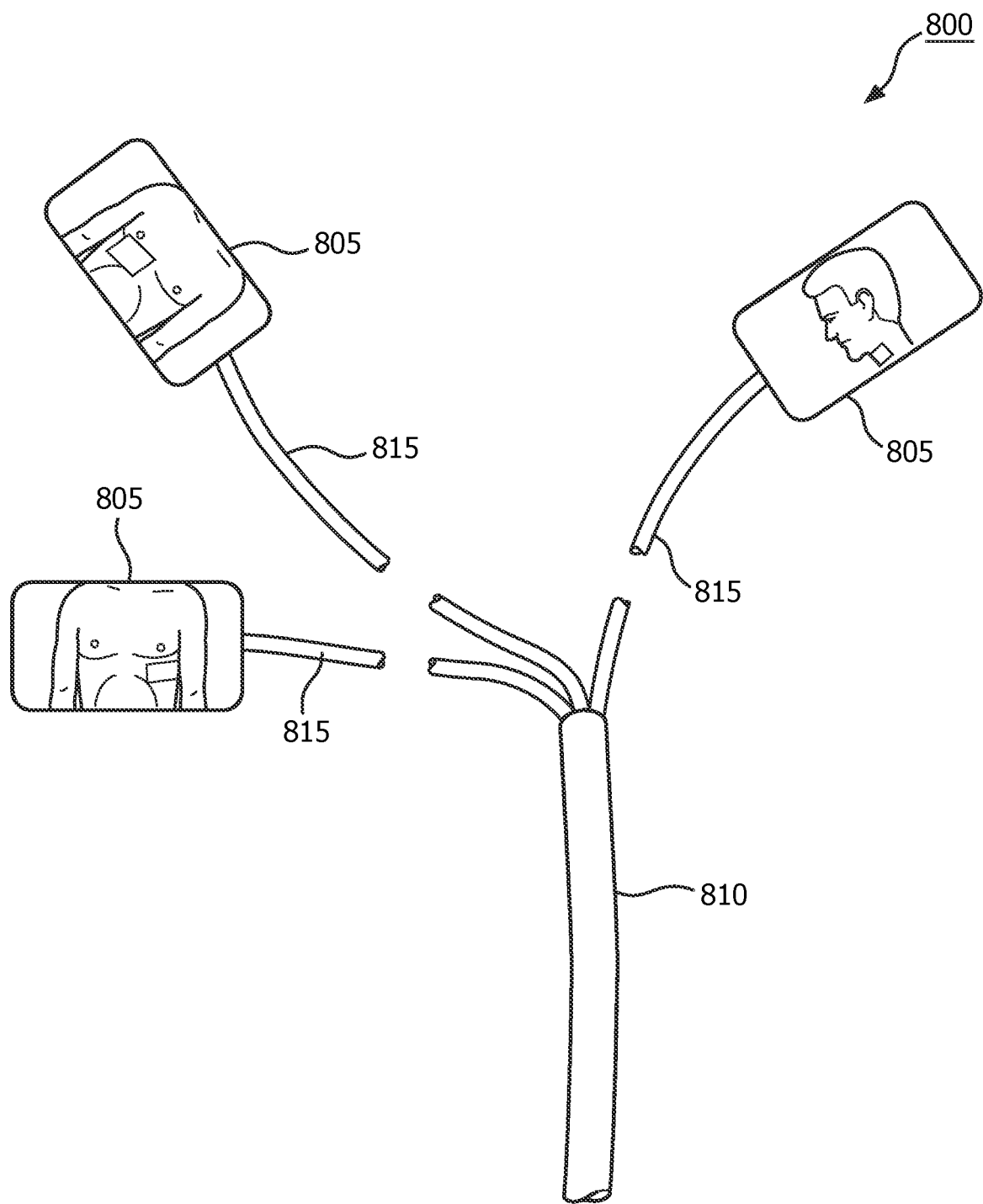
FIG. 8 is a schematic illustration of ultrasound probes according to an embodiment of the disclosure.

FIG. 8 shows a schematic illustration of ultrasound probes 800 according to an embodiment of the invention. The ultrasound probes 800 may be used with a portable CS device, such as portable device 500, 600, 700. The ultrasound probes may have graphics 805 applied to the surface facing an operator. The graphics 805 may illustrate the correct positions of the ultrasound probes 800 on a patient. This may further assist untrained operators in correctly placing the ultrasound probes 800. In some embodiments, a sheath 810 may be used to at least partially enclose the cables 815 that couple the ultrasound probes 800 to the portable device. This may prevent the operator from forgetting to apply one or more of the ultrasound probes 800. It may also reduce the chance of one or more of the ultrasound probes 800 being separated from the portable CS device.

In some embodiments, a portable CS device may be used concurrently with an automatic external defibrillator. In some embodiments, a portable device for delivering CS therapy may be packaged with an automatic external defibrillator (AED) for concurrent use. In some embodiments, CS therapy and defibrillation may be delivered to a patient in an alternating fashion. For example, the patient may be initially treated with external defibrillation and then CS therapy may be administered, or vice versa. The electrodes for the AED may be placed at different locations on a patient than the ultrasound probes. The ultrasound probes and electrodes may be configured to prevent interference between the two therapies. The combination of external defibrillation and CS therapy may improve patient outcomes for acute cardiac events that occur outside a clinical environment.

Figure 9:
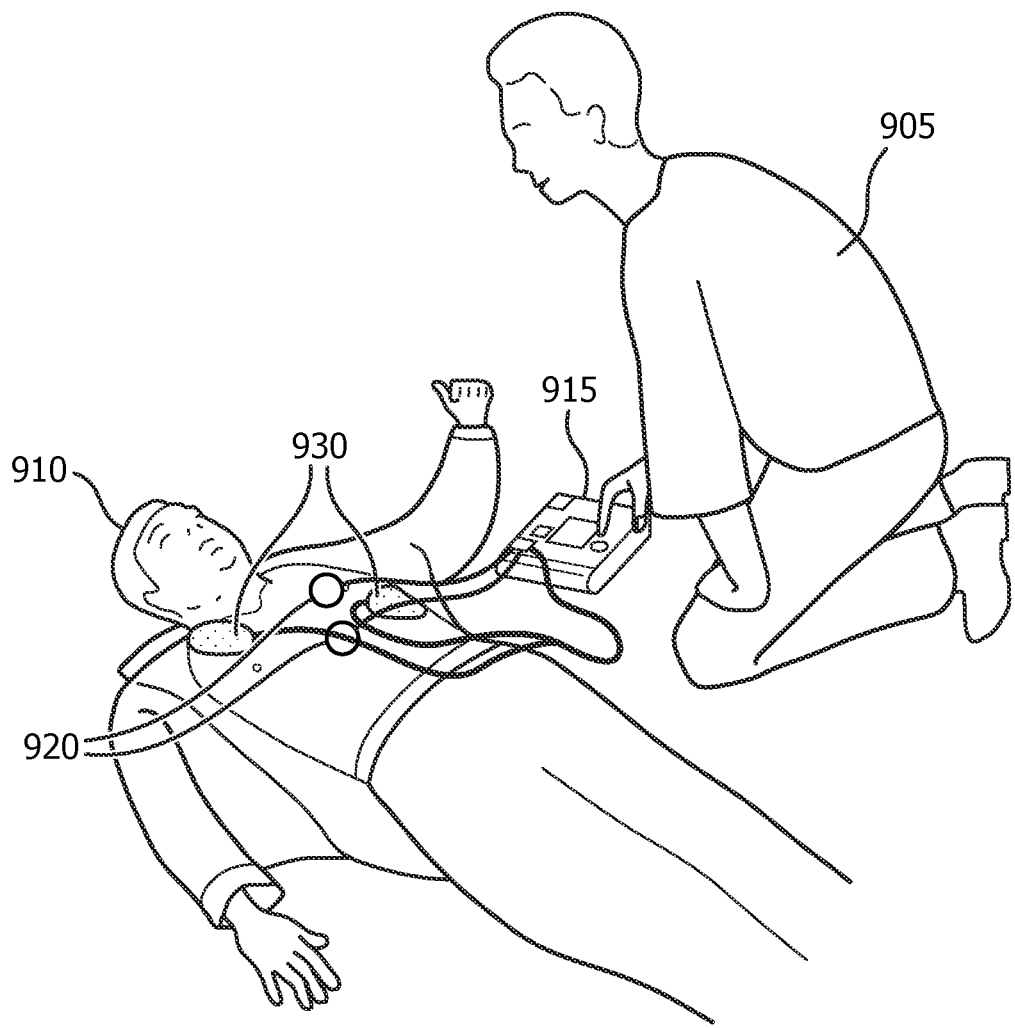
FIG. 9 is a schematic illustration of a combination cardiac sonothrombolysis-automatic external defibrillator device in use according to an embodiment of the disclosure.

FIG. 9 is a schematic illustration of an operator 905 providing CS therapy and defibrillation to a patient 910 according to an embodiment of the invention. The operator 915 may use a portable CS-AED combination device 915 coupled to ultrasound probes 920 and electrodes 930 that have been applied to the patient 910. The portable CS-AED combination device 915 may be implemented using one or more components of portable CS device 700 in some embodiments. The portable CS-AED combination device 915 may have a simplified user interface such that a person without medical training may provide aid to a patient experiencing an acute cardiac event before EMRs arrive in some embodiments.

Figure 10:
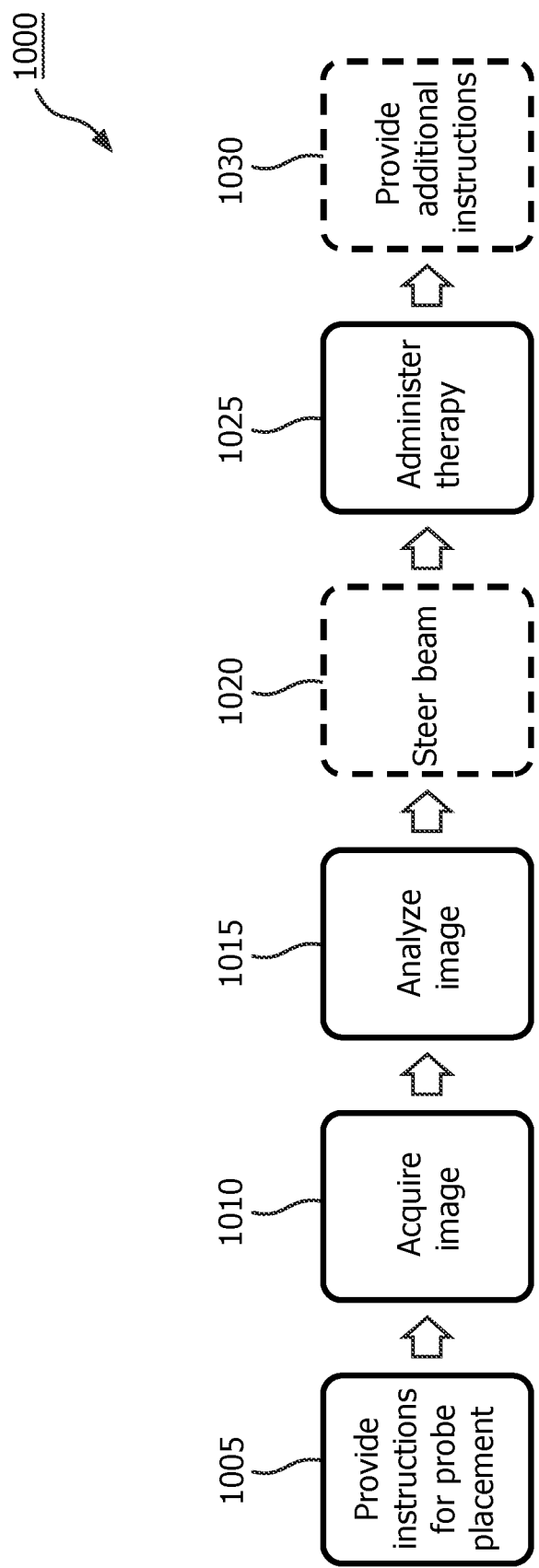
FIG. 10 is a flow chart of a method according to an embodiment of the disclosure.

FIG. 10 is a flow chart of an example process 1000 performed by a portable CS device, such as portable device 500, 600, and 700. First, the portable CS device may provide instructions to an operator for how to apply one or more ultrasound probes to a patient at Step 1005. The instructions may be provided visually and/or audibly. At Step 1010, one or more ultrasound probes may acquire an image of the patient. The image may be analyzed by a blockage detector processor and/or a heart recognition processor at Step 1015. If the analysis determines that the patient's heart is not adequately within the field of view of one or more of the ultrasound probes, the beam of one or more of the ultrasound probes may be steered at Step 1020 to achieve adequate imaging. If the beam cannot be steered to achieve an adequate field of view, the ultrasound system may alert the operator that one or more ultrasound probes need to be removed and reapplied. After the heart has been determined to be adequately within the field of view of the one or more ultrasound probes, the ultrasound probes may then deliver CS therapy to the patient at Step 1025. In some embodiments, during and/or after CS therapy is administered to the patient, the portable CS device may provide additional instructions to the operator at Step 1030. Instructions may be associated with modifying the therapy, additional treatment for the patient, and/or entering patient data for recording to a memory in the portable CS device. In some embodiments, the portable CS device may store the acquired image or images in the memory, even if no image is provided to the operator on a display.

Although not always shown, the displays, touch screens, and/or other user interfaces may also illustrate user selections which may include, for example, icons or menu items which may be selected by the user to, for example, scan, file, print, transfer images (e.g., from one display to another), mute, transcribe, and/or use a headpiece, as desired. Further, one or more menus as is known in the art may be provided for a user's convenience. The displayed images and associated data may be saved for subsequent physician analysis. However, a history mode may be activated to gather information indicative of when data may have been added and/or edited so that a user may refer back to original information and/or determine when and/or who made certain changes to information which may be saved in, for example, a generated report. Further, the changes may also be stored for later use.

Although the present system has been described with reference to a cardiac sonothrombolysis ultrasound system, it is also envisioned that the present system can be extended to other areas of the body where sonothrombolysis therapy may be desired. Accordingly, the present system may be used to obtain and/or record image information related to, but not limited to renal, testicular, breast, ovarian, uterine, thyroid, hepatic, lung, musculoskeletal, splenic, cardiac, arterial and vascular systems. Further, the present system may also include one or more programs which may be used with conventional imaging systems so that they may provide features and advantages of the present system.

Further, the present systems, apparatuses, and methods, may also be extended to any small parts imaging where low power ultrasound therapy may be delivered. Further, the present methods may be embedded in a program code which may be applied to existing imaging systems such as, for example, ultrasonic imaging systems. Suitable ultrasonic imaging systems may include a Philips® ultrasound system which may, for example, support a conventional broadband linear array transducer that may be suitable for small-parts imaging. Further, analysis techniques such as, for example, QLAB™ may be available on-cart with an imaging apparatus or as a post-processing program which may be run outside of an examination room. Further, multiple nodules, anatomical entities such as follicles, or other detectible objects, may be marked using the present system. Further, the method of the present systems may be applied to volumes acquired using transducers such as, for example, 2D array transducers, which may include, for example, X-matrix™ or mechanical transducers.

It will be understood that certain of the block diagram illustrations, and combinations of blocks in the block diagram illustrations, as well any portion of the systems and methods disclosed herein, can be implemented by computer program instructions. These program instructions may be provided to a processor to produce a machine, such that the instructions, which execute on the processor, create means for implementing the actions specified in the block diagram block or blocks or described for the systems and methods disclosed herein. The computer program instructions may be executed by a processor to cause a series of operational steps to be performed by the processor to produce a computer implemented process. The computer program instructions may also cause at least some of the operational steps to be performed in parallel. Moreover, some of the steps may also be performed across more than one processor, such as might arise in a multi-processor computer system. In addition, one or more processes may also be performed concurrently with other processes, or even in a different sequence than illustrated without departing from the scope or spirit of the invention.

The computer program instructions can be stored on any suitable computer-readable hardware medium including, but not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computing device. Furthermore, processors described herein, such as the heart recognition processor, can include one or more suitable data processor(s) that, for example, can include a suitable microprocessor, digital signal processor (DSP), image processor, or the like, such as an integrated circuit (e.g., a field-programmable gate array).

Certain additional advantages and features of this invention may be apparent to those skilled in the art upon studying the disclosure, or may be experienced by persons employing the novel system and method of the present invention, chief of which is that a more reliable cardiac sonothrombolysis device and method of operation thereof is provided. Another advantage of the present systems and method is that conventional medical image systems can be easily upgraded to incorporate the features and advantages of the present systems, devices, and methods.

Of course, it is to be appreciated that any one of the above embodiments or processes may be combined with one or more other embodiments and/or processes or be separated and/or performed amongst separate devices or device portions in accordance with the present systems, devices and methods.

Finally, the above-discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

What is claimed is:

1. A method, comprising:
   providing instructions for placing an ultrasound probe on a patient to a user;
   receiving a signal from the ultrasound probe configured to be removably coupled to the patient via an adhesive on the ultrasound probe;
   generating a two-dimensional ultrasound image or a three-dimensional ultrasound image from the signal;
   analyzing the two-dimensional ultrasound image or the three-dimensional ultrasound image with a blockage detector processor to determine if an object is blocking a field of view of the ultrasound probe;
   analyzing the two-dimensional ultrasound image or the three-dimensional ultrasound image with a heart recognition processor to determine if the ultrasound probe has a desired view of a heart;
   steering a beam of the ultrasound probe responsive to determining an object is blocking the field of view or the ultrasound probe does not have the desired view of the heart;
   and providing cardiac sonothrombolysis therapy with the ultrasound probe.

2. A method, comprising:
   providing instructions for providing a cardiac sonothrombolysis therapy with an ultrasound probe to a user;

receiving a signal from the ultrasound probe configured to be removably coupled to the patient via an adhesive on the ultrasound probe;

generating a two-dimensional ultrasound image or a three-dimensional ultrasound image from the signal;

analyzing the two-dimensional ultrasound image or the three-dimensional ultrasound image with a blockage detector processor to determine if an object is blocking a field of view of the ultrasound probe;

analyzing the two-dimensional ultrasound image or the three-dimensional ultrasound image with a heart recognition processor to determine if the ultrasound probe has a desired view of a heart;

steering a beam of the ultrasound probe responsive to determining an object is blocking the field of view or the ultrasound probe does not have the desired view of the heart; and providing cardiac sonothrombolysis therapy with the ultrasound probe.

3. The method of claim 1, further comprising providing external defibrillation with an electrode.

* * * * *